US008097862B2

(12) United States Patent
Kimura

(10) Patent No.: US 8,097,862 B2
(45) Date of Patent: *Jan. 17, 2012

(54) FLUORESCENCE DETECTING METHOD AND FLUORESCENCE DETECTING APPARATUS

(75) Inventor: Toshihito Kimura, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 324 days.

This patent is subject to a terminal disclaimer.

(21) Appl. No.: 12/400,322

(22) Filed: Mar. 9, 2009

(65) Prior Publication Data

US 2009/0230308 A1 Sep. 17, 2009

(30) Foreign Application Priority Data

Mar. 11, 2008 (JP) ................................. 2008-060435

(51) Int. Cl.
*G01J 1/58* (2006.01)
(52) U.S. Cl. .................................. 250/458.1; 250/461.1
(58) Field of Classification Search ............... 250/458.1, 250/461.1
See application file for complete search history.

(56) References Cited

U.S. PATENT DOCUMENTS

| 6,707,561 | B1 * | 3/2004 | Budach et al. ................ 356/521 |
| 2006/0127278 | A1 | 6/2006 | Gast et al. |
| 2009/0161104 | A1 * | 6/2009 | Schultz et al. ................ 356/317 |
| 2009/0242802 | A1 * | 10/2009 | Kimura ....................... 250/459.1 |

OTHER PUBLICATIONS

Margarida M. L. M. Vareiro, et al. "Surface Plasmon Fluorescence Measurements of Human Chorionic Gonadotrophin: Role of Antibody Orientation in Obtaining Enhanced Sensitivity and Limit of Detection", Analytical Chemistry, Apr. 15, 2005, pp. 2426-2431, vol. 77, No. 8.
European Search Report, corresponding to EP 09 003537, dated Aug. 31, 2010.

* cited by examiner

*Primary Examiner* — David Porta
*Assistant Examiner* — Christine Sung
(74) *Attorney, Agent, or Firm* — Sughrue Mion, PLLC

(57) ABSTRACT

Fluorescence detection utilizes surface plasmon. The intensity of scattered light, which is substantially proportionate to the intensity of an electric field enhancing field generated on a metal film, is employed, to normalize and correct the intensity of fluorescence emitted by fluorescent labels with respect to the intensity of the electric field enhancing field.

4 Claims, 3 Drawing Sheets

FLUORESCENCE DETECTING METHOD AND FLUORESCENCE DETECTING APPARATUS

BACKGROUND OF THE INVENTION

1. Field of the Invention

The present invention is related to a fluorescence detecting method and a fluorescence detecting apparatus that utilize surface plasmon. More specifically, the present invention is related to a fluorescence detecting method and a fluorescence detecting apparatus that utilizes a correcting mechanism to correct detected intensities of fluorescence.

2. Description of the Related Art

Conventionally, detecting methods that utilize totally reflected illumination are being focused on, in biological measurements for detecting proteins, DNA, and the like. These detection methods detect the presence or the amount of a detection target substance, by analyzing optical interactions such as scattering, absorption, and light emission, between light that leaks out when a measuring light beam is totally reflected at an interface between materials having different refractive indices, that is, evanescent waves, and the detection target substance, which is included in a sample, or labels attached to the detection target substance.

An example of such a detecting method is a fluorescence detecting method that utilizes fluorescent labels (refer to Margarida M. L. M. Vareiro, et al., "Surface Plasmon Fluorescence Measurements of Human Chorionic Gonadotrophin: Role of Antibody Orientation in Obtaining Enhanced Sensitivity and Limit of Detection", Analytical Chemistry, Vol. 77, No. 8, pp. 2426-2431, 2005.)

With recent advances in the performance of photodetectors, such as cooled CCD's, fluorometry has become indispensable in biological research. In addition, fluorescent pigments having fluorescence quantum yields that exceed 0.2, which is the standard for practical use, such as FITC (fluorescence: 525 nm, fluorescence quantum yield: 0.6) and Cy5 (fluorescence: 680 nm, fluorescence quantum yield: 0.3) have been developed as fluorescent labeling materials and are being widely used. Further, high sensitivity detection on the order of 1 pM and less is being realized, by amplifying fluorescence signals employing electric field enhancing fields due to surface plasmon.

The principles of the aforementioned fluorescence detecting method will be explained with reference to FIG. 3.

FIG. 3 is a conceptual diagram that illustrates a fluorescence detecting apparatus. For the sake of convenience in the explanation, the dimensions of each component are not drawn to actual scale.

The fluorescence detecting apparatus illustrated in FIG. 3 is equipped with: a sensor chip 10 constituted by a dielectric plate 11 and a metal film 12 provided at a predetermined region on one surface of the dielectric plate; an excitation light outputting optical system 20 that outputs an excitation light beam $L_0$ at an incident angle that satisfies conditions for total reflection at the interface between the dielectric plate 11 and the metal film 12 from the side of the sensor chip 10 opposite the surface on which the metal film 12 is formed; and a photodetector 30 that detects fluorescence Lf generated by fluorescent labels F, which are attached to a detection target substance A, in the case that the detection target substance A having the fluorescent labels F attached thereto are present in a sample S in contact with the metal film 12.

In this fluorescence detecting apparatus, the excitation light beam $L_0$ is output from the excitation light outputting optical system 20 and enters the interface between the dielectric plate 11 and the metal film 12 at a specific incident angle greater than or equal to a total reflection angle. Thereby, evanescent waves leak into the sample S on the metal film 12, and surface plasmon within the metal film 12 are excited by the evanescent waves. The evanescent waves and the surface plasmon cause an electric field enhancing field Ew that exhibits an electric field enhancing effect to be formed locally on the surface of the metal film 12.

A case will be considered in which antigens A are detected from within a sample S that includes the antigens A as a detection target substance. The metal film 12 is modified with primary antibodies B1 that specifically bind with the antigens A. The sample S is caused to flow into a sample holding section 13, and then secondary antibodies B2, which are modified with fluorescent labels F and that also specifically bind with the antigens A, are caused to flow into the sample holding section 13. At this time, the fluorescent labels F are immobilized to the metal film 12 via the specific bonds of the primary antibodies B1, the antigens A, and the secondary antibodies B2.

In the case described above, the fluorescent labels F are present within the electric field enhancing field Ew, and the fluorescent labels F are excited and caused to emit fluorescence Lf. Accordingly, the antigens A can be detected by detecting the fluorescence Lf. Note that the presence the fluorescent labels F is actually directly confirmed by the detection of fluorescence. However, it is considered that the fluorescent labels F would not be immobilized onto the metal film 12 unless the antigens A are present. Therefore, the presence of the antigens A is indirectly confirmed by confirming the presence of the fluorescent labels F.

However, in the aforementioned fluorescent detecting method, there are many factors that contribute to fluctuations in the intensity of the electric field enhancing field generated by surface plasmon. Therefore, it is difficult to completely uniformize all of the factors for each measurement. This causes a problem that detected intensities of fluorescence fluctuate, and that reproducibility is poor, even if the amounts of detection target substances within samples are the same. These factors include: margins of error in the shapes and settings of sensor chips; shifting in the incident angle of excitation light beams caused by human error such as margins of errors in sensing and margins of error in setup of the optical system; and shifting in surface plasmon generating conditions due to physical factors such as the refractive indices of samples, the refractive indices of the sensor chips, irregularities on the surfaces of the sensor chips, the thicknesses of the metal films, and the densities of the metal films. In addition, changes in environmental temperatures during measurement may also lead to shifting in the aforementioned conditions, and therefore must be considered as well.

Variations in the aforementioned factors can be suppressed by selecting or exchanging components for optimal components for each measurement. However, extreme amounts of trouble and cost will be incurred if variations in all of the factors are suppressed by selecting or exchanging components.

SUMMARY OF THE INVENTION

The present invention has been developed in view of the aforementioned problem. It is an object of the present invention to provide a fluorescence detecting method and a fluorescence detecting apparatus that can realize measurements having reproducibility, in which fluctuations in intensities of electric field enhancing fields that occur at each measurement are suppressed, simply and at low cost.

A fluorescence detecting method of the present invention comprises the steps of:

preparing a dielectric plate, and a metal film which is provided at a predetermined region on one surface of the dielectric plate, onto which a sample that includes a detection target substance and fluorescent labels is supplied;

irradiating an excitation light beam through the dielectric plate such that it enters the interface between the dielectric plate and the metal film, to cause an electric field enhancing field to be generated on the surface of the metal film;

detecting fluorescence emitted by the fluorescent labels due to excitation by the electric field enhancing field with a first photodetector; and detecting the amount of the detection target substance based on the intensity of fluorescence detected by the first photodetector; and is characterized by:

scattered light of the electric field enhancing field, which is substantially proportionate to the intensity of the electric field enhancing field, being detected with a second photodetector; and the intensity of fluorescence being normalized and corrected with respect to the intensity of the electric field enhancing field, employing the intensity of the scattered light detected by the second photodetector.

In the fluorescence detecting method of the present invention, it is preferable for a corrected intensity of fluorescence Ifc to be derived according to the following Formula (1), employing the detected intensity of fluorescence If and the detected intensity of scattered light Is.

$$Ifc = If/Is \qquad (1)$$

Here, the term "electric field enhancing field" refers to a local region on the upper surface of the metal film that exhibits an enhancing effect of electric fields, generated due to the evanescent waves which are generated by irradiating the excitation light beam onto the interface between the dielectric plate and the metal film such that conditions for total reflection are satisfied at the interface, and due to surface plasmon which are induced by the evanescent waves and generated within the metal film.

The phrase "intensity of fluorescence being normalized . . . with respect to the intensity of the electric field enhancing field" means that an intensity of fluorescence is determined to be a reference with respect to an arbitrary intensity of the electric field enhancing field, and relatively estimating actually measured intensities of fluorescence based on the reference intensity of fluorescence.

A fluorescence detecting apparatus of the present invention for detecting the amount of a detection target substance comprises:

a dielectric plate;

a metal film which is provided at a predetermined region on one surface of the dielectric plate, onto which a sample that includes the detection target substance and fluorescent labels is supplied;

a light source for irradiating an excitation light beam through the dielectric plate such that it enters the interface between the dielectric plate and the metal film, to cause an electric field enhancing field to be generated on the surface of the metal film; and a first photodetector for detecting the intensity of fluorescence generated by the excitation effect of the electric field enhancing field; characterized by further comprising:

a second photodetector for detecting scattered light of the electric field enhancing field, which is substantially proportionate to the intensity of the electric field enhancing field; and a correcting mechanism, for normalizing and correcting the intensity of fluorescence with respect to the intensity of the electric field enhancing field, employing the intensity of the scattered light detected by the second photodetector; and the amount of the detection target substance being detected based on the intensity of fluorescence detected by the first photodetector, which has been corrected by the correcting mechanism.

In the fluorescence detecting apparatus of the present invention, it is preferable for the correcting mechanism to derive a corrected intensity of fluorescence Ifc according to the following Formula (1), employing the detected intensity of fluorescence If and the detected intensity of scattered light Is.

$$Ifc = If/Is \qquad (1)$$

Note that in the fluorescence detecting method and the fluorescence detecting apparatus of the present invention, the phrase "detecting the amount of a detection target substance" refers not only to detecting quantitative amounts of the detection target substance, but qualitatively detecting whether the detection target substance is present. The phrase also refers to detection of degrees of activity of the detection target substance.

In the fluorescence detecting method and the fluorescence detecting apparatus of the present invention, the intensity of fluorescence detected in each measurement is corrected based on the intensity of light which is scattered by the electric field enhancing field generated by irradiation of the excitation light. The intensity of fluorescence and the intensity of scattered light are both dependent on the generated state of the electric field enhancing field. In addition, the generated state of the electric field enhancing field is dependent on the measurement environment. Accordingly, the scattered light, the intensity of which is substantially proportionate to the intensity of the electric field enhancing field, is employed as an index of the generated state of the electric field enhancing field. Thereby, it becomes possible to normalize and correct the intensity of fluorescence with respect to the intensity of the electric field enhancing field. Therefore, correction suited to conditions can be performed for each measurement, and the factors that contribute to fluctuations in the intensity of the electric field enhancing effect that occur during each measurement can be suppressed. Accordingly, measurements having reproducibility can be realized simply and at low cost, without selecting or exchanging components to be optimal for each measurement.

BEST MODE FOR CARRYING OUT THE INVENTION

Hereinafter, an embodiment of the present invention will be described with reference to the drawings. However, the present invention is not limited to the embodiment to be described below.

<Fluorescence Detecting Method and Fluorescence Detecting Apparatus>

Figure 1:
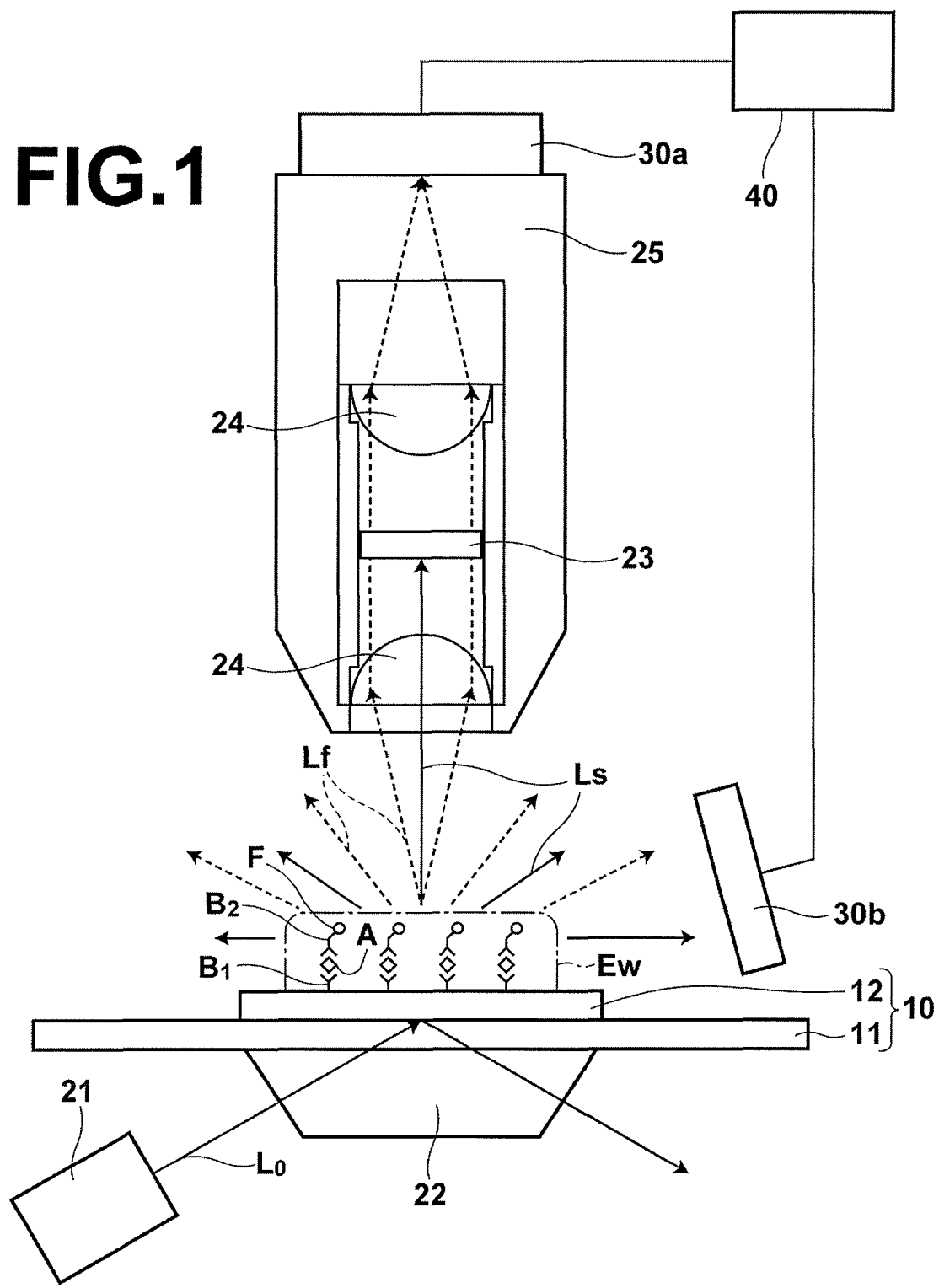
FIG. 1 is a schematic sectional view that illustrates a first fluorescence detecting apparatus of the present invention.

FIG. 1 is a schematic diagram that illustrates a fluorescence detecting apparatus according to a first embodiment of the present invention.

As illustrated in FIG. 1, the fluorescence detecting apparatus is equipped with: a sensor chip 10 constituted by a dielectric plate 11 and a metal film 12; a light source 21 that emits an excitation light beam $L_0$ of a predetermined wavelength which is capable of exciting fluorescent labels F; a prism 22, on which the sensor chip 10 is placed; a first photodetector 30a for detecting fluorescence Lf emitted by the fluorescent labels F which are supplied onto the sensor chip 10; two planoconvex lenses 24 which are arranged so as to guide the fluorescence Lf to the first photodetector 30a; an optical filter 23 provided between the two planoconvex lenses 24, for cutting off scattered light Ls scattered by an electric field enhancing filed Ew; a second photodetector 30b arranged so as to detect the scattered light Ls; and a personal computer 40 (PC 40) connected to the first photodetector 30a and the second photodetector 30b. Here, the light source 21 is provided toward the side of the prism 22 from the dielectric plate 11, such that the electric field enhancing field Ew is generated on the sensor chip 10. The fluorescent labels F are immobilized onto the metal film 12 via primary antibodies B1, antigens A and secondary antibodies B2. The PC 40 has a correcting mechanism, for normalizing and correcting the intensity of fluorescence with respect to the intensity of the electric field enhancing field Ew, employing the intensity of the scattered light Ls. In addition, reference numeral 25 in FIG. 1 denotes an optical system holding portion, in which the two planoconvex lenses 24 and the optical filter 23 are contained, and to which the first photodetector 30a is mounted.

Figure 3:
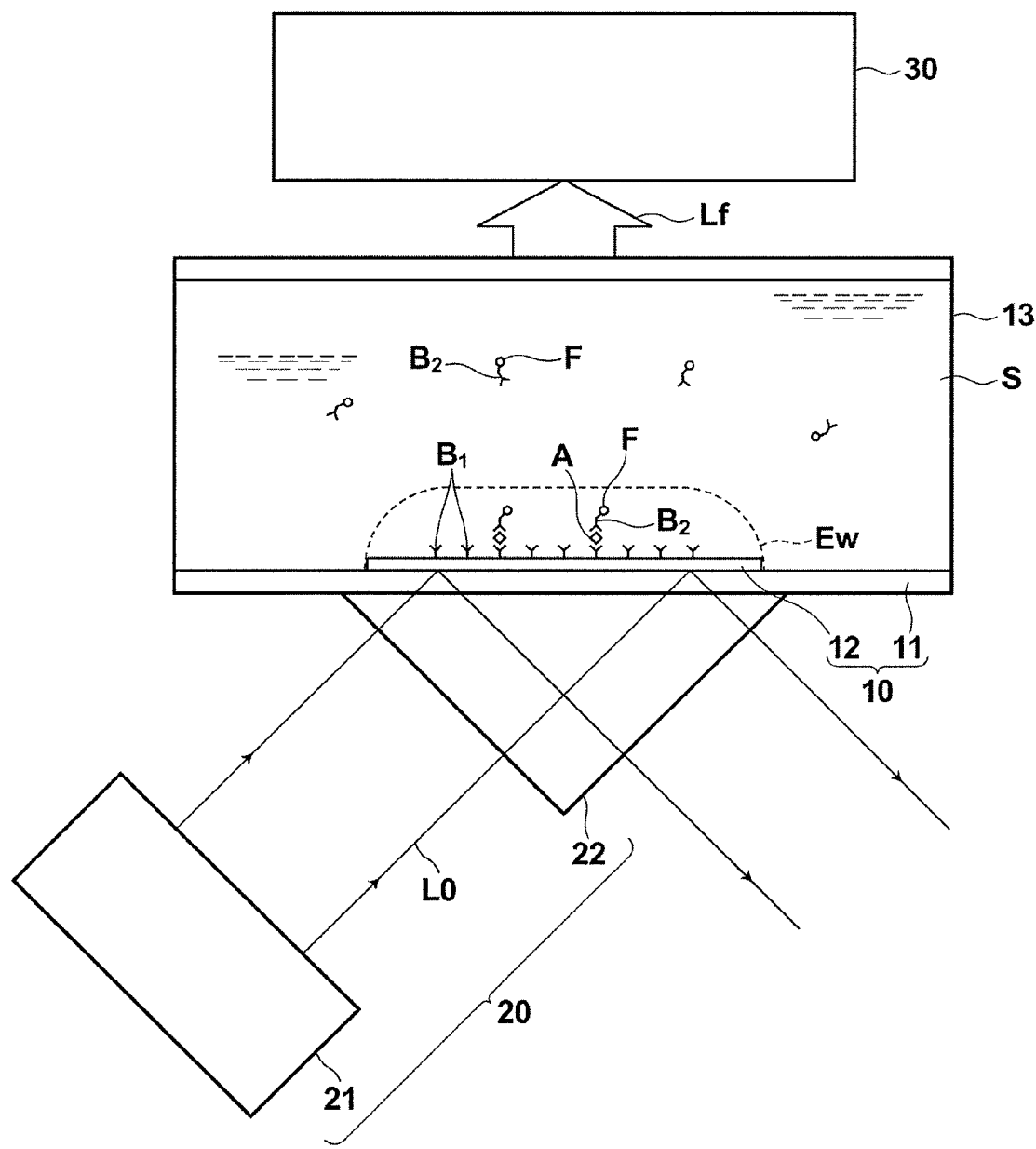
FIG. 3 is a schematic sectional view that illustrates a fluorescence detecting apparatus that employs a conventional fluorescence detecting method.

The sensor chip 10 is not particularly limited, and may be the same sensor chip 10 as described previously with reference to FIG. 3. The sensor chip 10 is constituted by the metal film 12, which is formed on a predetermined region of a surface of the dielectric plate 11.

The dielectric plate 11 may be formed by transparent materials such as transparent resins and glass. It is desirable for the dielectric plate 11 to be formed by resin. In the case that the dielectric plate 11 is formed by resin, polymethyl methacrylate (PMMA), polycarbonate (PC), and non crystalline polyolefin (APO) that includes cycloolefin may be favorably employed.

The metal film 12 may be formed by known vapor deposition methods. The thickness of the metal film 12 is preferably set appropriately according to the material of the metal film 12 and such that surface plasmon is strongly excited by the wavelength of the excitation light beam $L_0$. For example, in the case that a laser beam having a central wavelength of 780 nm is employed as the excitation light beam $L_0$ and a gold (Au) film is employed as the metal film 12, a favorable thickness of the metal film 12 is 50 nm±5 nm. Note that it is preferable for the metal film 12 to have at least one metal selected from among a group consisting of Au, Ag, Cu, Pt, Ni, Ti, and alloys thereof as a main component.

Note that a sample holding section for holding liquid samples may be provided on the sensor chip 10, and the sensor chip 10 and the sample holding section may constitute a box shaped cell, which is capable of holding liquid samples. On the other hand, in cases that extremely small amounts of liquid samples, to a degree which can be held on the sensor chip 10 by surface tension, are to be measured, the sensor chip 10 may not be provided with the sample holding section.

The prism 22 guides the excitation light beam $L_0$ such that the excitation light beam $L_0$ is totally reflected at the interface between the dielectric plate 11 and the metal film 12. Note that the prism 22 and the dielectric plate 11 are in contact via a refractive index matching oil.

The light source 21 is not particularly limited, and may be a laser light source. The type of light source to be employed as the light source 21 may be appropriately selected according to detection conditions. As described previously, the light source 21 is arranged such that the excitation light beam $L_0$ output thereby enters the interface between the dielectric plate 11 and the metal film 12 at a specific angle that causes total reflection at the interface, and such that surface plasmon resonance occurs at the metal film 12. Further, a light guiding member may be provided between the light source 21 and the prism 22 as necessary. Note that it is preferable for the excitation light beam $L_0$ to enter the interface in a P polarized state, such that surface plasmon can be induced.

The excitation light beam $L_0$ is not particularly limited, and may be a single wavelength light beam emitted from a laser light source or the like, or a broad spectrum light beam emitted from a white light source. The type of light beam to be employed as the excitation light beam $L_0$ may be appropriately selected according to detection conditions.

The first photodetector 30a is not limited, as long as it is capable of quantitatively detecting the fluorescence Lf emitted by the fluorescent labels F included in the sample S. The first photodetector 30a may be selected appropriately according to detection conditions. Examples of photodetectors to be employed as the first photodetector 30a include: CCD's, PD's (photodiodes); photomultipliers; and c-MOS's. In addition, the photodetector may be employed in combination with light dividing means, such as an optical filter or a spectroscope, according to detection conditions. Note that LAS-1000 manufactured by FUJIFILM Corporation is an example of an apparatus equipped with the optical system holding section 25, the two planoconvex lenses 24, the optical filter 23 and the photodetector 30a, and can be favorably employed.

Figure 2:
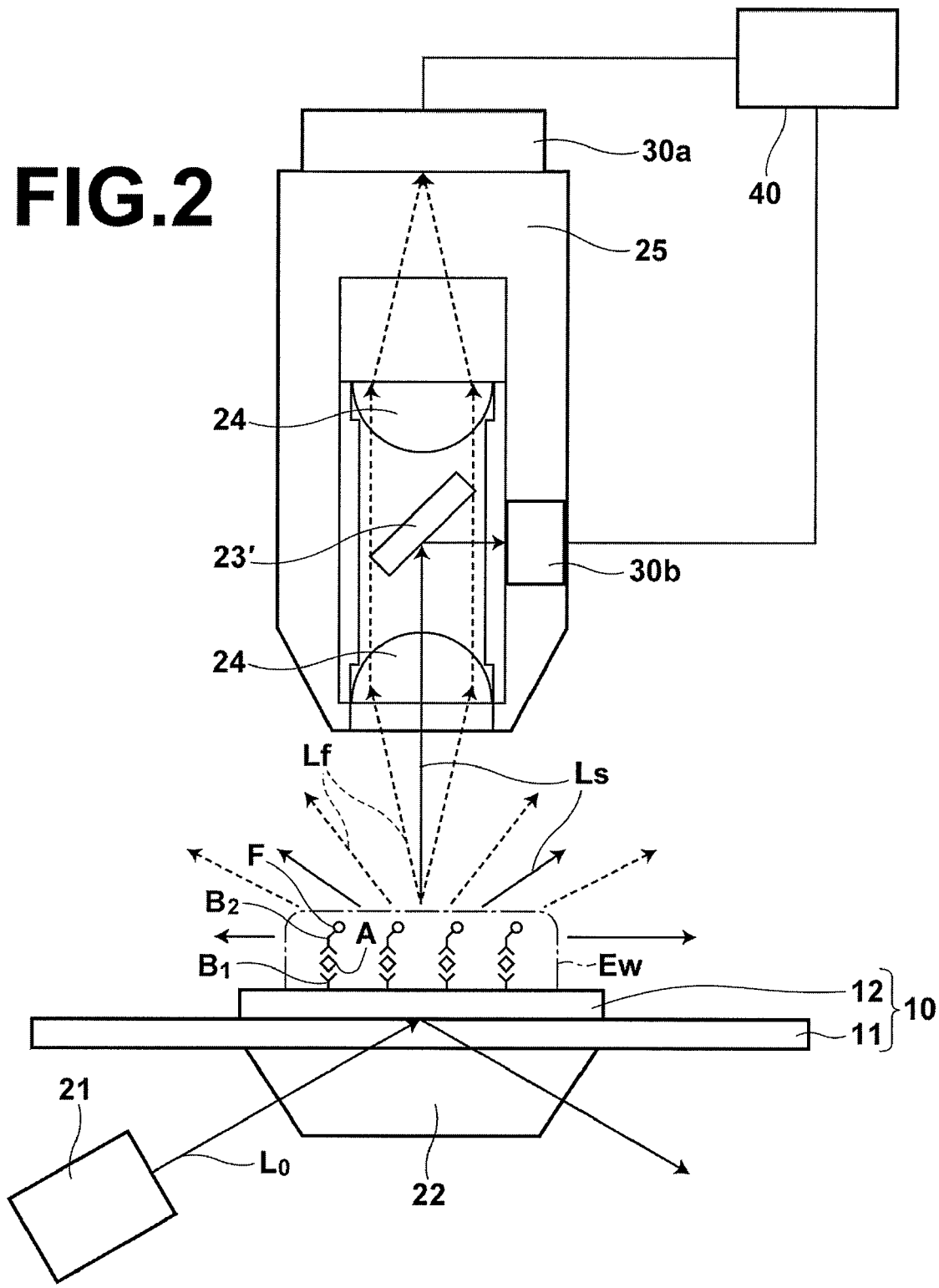
FIG. 2 is a schematic sectional view that illustrates a second fluorescence detecting apparatus of the present invention.

The second photodetector 30b may similarly be selected appropriately according to detection conditions. Examples of photodetectors to be employed as the second photodetector 30b include: CCD's, PD's (photodiodes); photomultipliers; and c-MOS's. In addition, the photodetector may be employed in combination with light dividing means, such as an optical filter or a spectroscope, according to detection conditions. It is preferable for the second photodetector 30b to detect the scattered light Ls at a position along the propagating direction of evanescent waves (toward the right side in FIG. 1), as illustrated in FIG. 1. Thereby, it becomes possible to efficiently detect the scattered light Ls having directionality according to Mie scattering. Note that the second photodetector 30b may be built in to the interior of the optical system holding section 25, as illustrated in FIG. 2. In this case, a dichroic mirror 23' is employed instead of the aforementioned optical filter 23, to enable efficient detection of the fluorescence Lf and the scattered light Ls.

The PC 40 functions as a correcting mechanism that normalizes and corrects the intensity of fluorescence with respect to the intensity of the electric field enhancing field Ew, using the intensity of the scattered light Ls, which is substantially proportionate to the intensity of the electric field enhancing field Ew. Note that the correcting mechanism is not limited to being a personal computer, and may be any electronic calculator or the like, as long as the correcting mechanism serves the functions thereof.

Hereinafter, the fluorescence detecting method of the present invention will be described for a case in which the fluorescence detecting apparatus described above is employed to detect antigens A from within a sample S that includes the antigens A.

The light source 21 of the fluorescence detecting apparatus emits the excitation light beam $L_0$ such that it enters the interface between the dielectric plate 11 and the metal film 12 at a specific incident angle greater than or equal to a total reflection angle. Thereby, evanescent waves leak into the sample S on the metal film 12, and surface plasmon within the metal film 12 are excited by the evanescent waves. The evanescent waves and the surface plasmon cause an electric field enhancing field Ew that exhibits an electric field enhancing effect to be formed locally on the surface of the metal film 12.

A case will be considered in which antigens A are detected from within a sample S that includes the antigens A as a detection target substance. The metal film 12 is modified with primary antibodies B1 that specifically bind with the antigens A. The sample S is caused to flow into a sample holding section 13, and then secondary antibodies B2, which are modified with fluorescent labels F and that also specifically bind with the antigens A, are caused to flow into the sample holding section 13. At this time, the fluorescent labels F are immobilized to the metal film 12 via the specific bonds of the primary antibodies B1, the antigens A, and the secondary antibodies B2.

In the case described above, the fluorescent labels F are present within the electric field enhancing field Ew, and the fluorescent labels F are excited and caused to emit fluorescence Lf. In theory, it is possible to calculate the amount of the detection target substance present in the sample S using the intensity of the fluorescence. However, margins of error in the shapes and settings of sensor chips; shifting in the incident angle of excitation light beams caused by human error such as margins of errors in sensing and margins of error in setup of the optical system; and shifting in surface plasmon generating conditions due to physical factors such as the refractive indices of samples, the refractive indices of the sensor chips, irregularities on the surfaces of the sensor chips, the thicknesses of the metal films, and the densities of the metal films, cause fluctuations to occur in the intensity of the electric field enhancing field Ew. Accordingly, correction becomes necessary.

Therefore, the scattered light Ls of the electric field enhancing field Ew, which is generated due to irregularities in the surface of the dielectric plate 11 and the surface of the metal film 12, is employed to correct the intensity of fluorescence. The correction is performed by normalizing the intensity of fluorescence If with respect to the intensity of the electric field enhancing field Ew, using the intensity Is of the scattered light Ls, which is substantially proportionate to the intensity of the electric field enhancing field Ew. This correction is possible, because the percentage of light which is scattered at the electric field enhancing field Ew does not vary due to the aforementioned shifts in the incident angle of the excitation light beam $L_0$ or the shifts in the surface plasmon generating conditions. Further, the intensity Is of scattered light is substantially proportionate to the intensity of the electric field enhancing field Ew. Therefore, the intensity Is of scattered light serves as an index for estimating the intensity of the electric field enhancing field Ew.

Hereinafter, examples of the correcting method will be described with reference to Table 1 below, and the operation of the fluorescence detecting method and the fluorescence detecting apparatus of the present invention will be described.

TABLE 1

| | Measured Intensity of Scattered Light | Measured Intensity of Fluorescence | Corrected Intensity of Fluorescence (amount of detection target substance) |
|---|---|---|---|
| Case 1 | 1 | 1 | 1 |
| Case 2 | 0.5 | 0.5 | 1 |
| Case 3 | 0.5 | 1 | 2 |
| Case 4 | 2 | 1 | 0.5 |

The above table indicates actual measured values of the intensity of scattered light and the intensity of fluorescence for four samples (Case 1 through Case 4), as well as corrected intensities of fluorescence, which were calculated using the actual measured values. Note that the numerical values indicated in Table 1 are relative values that use Case 1 as a reference (with no unit of quantity).

First, Case 2 will be considered. In Case 2, the actual measured values for the intensity of scattered light and the intensity of fluorescence are 0.5 and 0.5, respectively. The actual measured value for the intensity of fluorescence in Case 2 is half that of Case 1, that is, 0.5. However, it can be seen that the intensity of scattered light is also half that of Case 1. These measured values suggest that shifts in the incident angle of the excitation light beam $L_0$ or shifts in surface plasmon generating conditions have halved the intensity of the electric field enhancing field itself. Because Case 1 is used as a reference, it becomes necessary to normalize and correct the intensity of fluorescence If with respect to the intensity of the electric field enhancing field Ew. As a specific method for this correction, Formula (1) below may be employed. Formula (1) takes advantage of the fact that the intensity of scattered light is substantially proportionate to the intensity of the electric field enhancing field Ew. In Formula (1), Ifc, If, and Is represent the corrected intensity of fluorescence, the actual measured value for the intensity of fluorescence, and the actual measured value for the intensity of scattered light, respectively.

$$Ifc = If/Is \qquad (1)$$

In the case that Formula (1) is employed, the corrected intensity of fluorescence for Case 2 becomes 1. Thereby, a result that the amount of the detection target substance which is present in the sample of Case 2 is approximately equal to that in the sample of Case 1 can be obtained.

Next, Case 3 will be considered. In Case 3, the actual measured values for the intensity of scattered light and the intensity of fluorescence are 0.5 and 1, respectively. The actual measured value for the intensity of fluorescence in Case 3 is equivalent to that of Case 1. However, the intensity of scattered light is half that of Case 1, that is, 0.5. These measured values suggest that shifts in the incident angle of the excitation light beam $L_0$ or shifts in surface plasmon generating conditions have halved the intensity of the electric field enhancing field itself. Because Case 1 is used as a reference, it becomes necessary to normalize and correct the intensity of fluorescence If with respect to the intensity of the electric field enhancing field Ew. If correction is administered using Formula (1) as for Case 2, the corrected intensity of fluorescence becomes 2. Thereby, a result that the amount of the detection target substance which is present in the sample of Case 3 is approximately two times that in the sample of Case 1 can be obtained.

Further, Case 4 will be considered. In Case 4, the actual measured values for the intensity of scattered light and the intensity of fluorescence are 2 and 1, respectively. The actual measured value for the intensity of fluorescence in Case 3 is equivalent to that of Case 1. However, the intensity of scattered light is double that of Case 1, that is, 2. These measured values suggest that unlike Case 2 and Case 3, measurement was performed under favorable conditions, in which adverse effects due to shifts in the incident angle of the excitation light beam $L_0$ or shifts in surface plasmon generating conditions were not present, and as a result, the intensity of the electric field enhancing field itself was doubled. Because Case 1 is used as a reference, it becomes necessary to normalize and correct the intensity of fluorescence If with respect to the intensity of the electric field enhancing field Ew. If correction is administered using Formula (1) as for the previous cases, the corrected intensity of fluorescence becomes 0.5. Thereby, a result that the amount of the detection target substance which is present in the sample of Case 4 is approximately half that in the sample of Case 1 can be obtained.

Note that in the examples described above as Case 1 through Case 4, one of the cases was used as a reference to evaluate the other cases in a relative manner. Alternatively, it is possible to produce calibration data in advance using a plurality of calibrating samples, for which the amount of detection target substances included therein are known. In this case, the amount of detection target substances can be evaluated in an absolute manner.

As described above, factors that cause fluctuations in intensities of electric field enhancing fields that occur at each measurement are suppressed. Therefore, measurements having reproducibility can be realized simply and at low cost, without selecting or exchanging optimal components for each measurement.

Note that a case has been described in which the correcting mechanism employs the scattered light Ls of the electric field enhancing field Ew. Similar advantageous effects can be obtained by monitoring the polarization states of a reflected excitation light beam and the fluorescence.

What is claimed is:

1. A fluorescence detecting method, comprising the steps of:

preparing a dielectric plate, and a metal film which is provided at a predetermined region on one surface of the dielectric plate, onto which a sample that includes a detection target substance and fluorescent labels is supplied;

irradiating an excitation light beam through the dielectric plate such that it enters the interface between the dielectric plate and the metal film, to cause an electric field enhancing field to be generated on the surface of the metal film;

detecting fluorescence emitted by the fluorescent labels due to excitation by the electric field enhancing field with a first photodetector;

detecting the amount of the detection target substance based on the intensity of fluorescence detected by the first photodetector;

detecting scattered light of the electric field enhancing field, which is substantially proportionate to the intensity of the electric field enhancing field, with a second photodetector; and normalizing and correcting the intensity of fluorescence with respect to the intensity of the electric field enhancing field, employing the intensity of the scattered light detected by the second photodetector.

2. A fluorescence detecting method as defined in claim 1, wherein:

a corrected intensity of fluorescence Ifc is derived according to the following Formula (1), employing the detected intensity of fluorescence If and the detected intensity of scattered light Is $$Ifc = If/Is \tag{1}$$

3. A fluorescence detecting apparatus, for detecting the amount of a detection target substance, comprising:

a dielectric plate;

a metal film which is provided at a predetermined region on one surface of the dielectric plate, onto which a sample that includes the detection target substance and fluorescent labels is supplied;

a light source for irradiating an excitation light beam through the dielectric plate such that it enters the interface between the dielectric plate and the metal film, to cause an electric field enhancing field to be generated on the surface of the metal film;

a first photodetector for detecting the intensity of fluorescence generated by the excitation effect of the electric field enhancing field;

a second photodetector for detecting scattered light of the electric field enhancing field, which is substantially proportionate to the intensity of the electric field enhancing field; and a correcting mechanism, for normalizing and correcting the intensity of fluorescence with respect to the intensity of the electric field enhancing field, employing the intensity of the scattered light detected by the second photodetector;

the amount of the detection target substance being detected based on the intensity of fluorescence detected by the first photodetector, which has been corrected by the correcting mechanism.

4. A fluorescence detecting apparatus as defined in claim 3, wherein:

the correcting mechanism derives a corrected intensity of fluorescence Ifc according to the following Formula (1), employing the detected intensity of fluorescence If and the detected intensity of scattered light Is $$Ifc = If/Is \tag{1}$$

* * * * *